(12) United States Patent
Zhang et al.

(10) Patent No.: US 12,083,162 B2
(45) Date of Patent: Sep. 10, 2024

(54) UNIVERSAL NANOSPONGE FOR TREATING RESPIRATORY VIRAL INFECTION

(71) Applicant: The Regents of the University of California, Oakland, CA (US)

(72) Inventors: Liangfang Zhang, San Diego, CA (US); Weiwei Gao, La Jolla, CA (US); Ronnie H. Fang, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 418 days.

(21) Appl. No.: 17/208,228

(22) Filed: Mar. 22, 2021

(65) Prior Publication Data

US 2021/0299217 A1     Sep. 30, 2021

Related U.S. Application Data

(60) Provisional application No. 62/994,069, filed on Mar. 24, 2020.

(51) Int. Cl.
*A61K 38/17*    (2006.01)
*A61K 9/127*    (2006.01)
*A61K 47/69*    (2017.01)

(52) U.S. Cl.
CPC .......... *A61K 38/1796* (2013.01); *A61K 9/127* (2013.01); *A61K 47/6901* (2017.08)

(58) Field of Classification Search
None
See application file for complete search history.

(56) References Cited

U.S. PATENT DOCUMENTS

2013/0337066 A1 * 12/2013 Zhang .................... A61K 9/148
                                                    424/234.1

FOREIGN PATENT DOCUMENTS

WO    WO-2017120342 A1 *  7/2017    ............. A61K 35/39

OTHER PUBLICATIONS

Yi et al (Int. J. Biol. Sci. 2020, vol. 16, pp. 1753-1766). (Year: 2020).*
Jia et al (Journal of Virology, 79(23), 2005, 14614-14621). (Year: 2005).*

* cited by examiner

*Primary Examiner* — Celeste A Roney
(74) *Attorney, Agent, or Firm* — Eversheds Sutherland (US) LLP (57) ABSTRACT

A nanoparticle comprising an outer surface comprising a plasma membrane derived from a cell that can be infected with a respiratory virus, including a human lung epithelial cell expressing ACE-2 receptor. Methods of manufacture and use for preventing or treating viral infections, such as coronavirus infection in a subject in need are disclosed.

20 Claims, 1 Drawing Sheet

UNIVERSAL NANOSPONGE FOR TREATING RESPIRATORY VIRAL INFECTION

CROSS REFERENCE TO RELATED APPLICATIONS

This application claims the priority benefit of U.S. Provisional Application No. 62/994,069, filed Mar. 24, 2020, which application is incorporated herein by reference.

GOVERNMENT SUPPORT

The invention was made with government support under Grant No. HDTRA1-18-1-0014 awarded by the Defense Threat Reduction Agency. The government has certain rights in the invention.

TECHNICAL FIELD

The present invention relates to a universal nanosponge for treating coronavirus infection.

BACKGROUND

There are currently no U.S. approved clinical therapeutics against coronavirus infections, and vaccines have also not yet been developed. There is some evidence that small molecule antiviral drugs can lessen disease burden, but these findings have not been validated. Previously, nanosponges have been proposed to work by physically neutralizing a pathogen, enabling the pathogen to be effectively cleared by the immune system. The closest analog that has been investigated for viral infections is passive immunization using antibodies directed against virus proteins. In contrast to this type of antibody therapy, which requires information about the precise antigenic material that is to be targeted, it would be desirable to have a system that works broadly by interrupting the mechanism by which the viruses use for cell binding and entry. For example, it has been shown that the novel coronavirus SARS-CoV-2 causing COVID-19 enters cells by interacting with angiotensin-converting enzyme 2 (ACE-2) found on respiratory cells.

SUMMARY OF THE INVENTION

The disclosure provides a new nanotechnology platform for treating coronavirus and other respiratory virus infections. The main active component of the platform is the plasma membrane derived from cells that are normally infected by coronaviruses or other respiratory viruses. The membrane is used to fabricate nanoscale particles, termed "nanosponges," that can be easily administered via a number of different routes to patients. The nanosponges are capable of binding to and neutralizing viruses because they express the surface receptors employed by the viruses for cellular entry. Notably, this approach when applied to coronavirus treatment does not depend on preexisting knowledge of the molecular structure of individual coronaviruses. Instead, the working mechanism (receptor-mediated cellular entry) of all coronaviruses can be broadly targeted, thus providing a generalized solution against new outbreaks of coronavirus.

There is some evidence that small molecule antiviral drugs can lessen coronavirus disease burden, but these findings have not been validated. The present nanosponges work by physically neutralizing the virus, enabling the pathogen to be effectively cleared by the immune system. Cell membrane particles derived from cell lines or engineered cells that are rich in ACE-2 can therefore be used to treat COVID-19. In fact, nanosponges with activity against new coronavirus strains can be developed even before identification of a specific receptor, as long as the targeted host cells are known. The disclosed technology can be applied broadly to any currently known or future emerging coronavirus, including but not limited to, SARS, MERS, SARS-CoV-2. As long as the virus is a coronavirus, the nanosponges will bind to the host cells in the lungs (e.g. lung epithelial cells and macrophages) and neutralize the virus. Nanosponges can be manufactured in advance using the appropriate cell membrane and stockpiled by pharmaceutical companies or governments to prepare for potential outbreaks. Production can also be rapidly scaled up in the event of an outbreak using commercially available techniques for large-scale cell culture.

Because it has been shown that the novel coronavirus SARS-CoV-2 causing COVID-19 enters cells by interacting with angiotensin-converting enzyme 2 (ACE-2) found on respiratory cells. Cell membrane particles derived from cell lines or engineered cells that are rich in ACE-2 can therefore be used to treat COVID-19. In fact, nanosponges with activity against new coronavirus strains can be developed even before identification of a specific receptor, as long as the targeted host cells are known.

To fabricate nanosponges, the plasma membrane is collected from a source cell, normally by a differential centrifugation process. In this case, the source cell would be a host cell that is normally infected by coronavirus (i.e. a lung epithelial cell expressing ACE-2). Although other respiratory viruses may bind to a different receptor than ACE-2, they will bind to some receptor(s) on the lung cell surface. Thus, ACE-2 is not the only receptor that may be used to identify a source cell. The cell can also be further modified by genetic engineering to overexpress a receptor of interest. The membrane can be either naturally occurring or modified. Modified membranes include any type of modified membrane, such as (i) genetically engineered cell membrane; (ii) physically and/or chemically modified cell membrane; and/or (iii) hybrid membranes consisting of some natural cellular membrane and some synthetic lipid membranes. The membrane material is processed into a nanoparticle by a process such as extrusion, sonication, or microfluidization, among others. It is possible to include a synthetic core within the center of the nanostructure, which can be used to load therapeutic payloads, including small molecule drugs, peptides, nucleic acids, and proteins, among many others. These nanoparticles can be stored frozen, either in solution or after lyophilization, and thawed or re constituted when treatment is required.

Nanosponges work by displaying the same surface markers that the coronavirus normally uses to enter a host cell. Upon binding to the nanosponge, the coronavirus can no longer interact with healthy host cells, thus reducing their ability to propagate infections. The nanosponge-virus complex will then be taken up by phagocytic cells and safely broken down within the endolysosomal compartment. Due to their nanoscale size, nanosponges can be safely administered by a number of different routes, including subcutaneously, intradermally, intravenously, intratracheally, and intranasally, among others.

In embodiments, the invention provides a nanoparticle comprising an outer surface comprising a plasma membrane derived from a cell, including a lung epithelia cell expressing ACE-2 receptor, that can be infected by a respiratory virus, including a coronavirus. Methods of manufacture and use for preventing or treating respiratory viral infection, and specifically coronavirus infection in a subject in need are disclosed.

In embodiments, the nanoparticle further comprising an inner core comprising a non-cellular material. In embodiments, the cellular membrane is derived from a human lung epithelial cell. In embodiments, the cellular membrane comprises angiotensin-converting enzyme 2 (ACE-2) receptors.

In embodiments, the nanoparticle further comprises a releasable cargo. In embodiments, the releasable cargo is a therapeutic agent, a prophylactic agent, a diagnostic or marker agent, a prognostic agent, or a combination thereof.

In embodiments, the invention provides medicament delivery systems, which comprising an effective amount of the nanoparticle described herein.

In embodiments, the invention provides pharmaceutical compositions comprising an effective amount of the nanoparticle described herein and a pharmaceutically acceptable carrier or excipient.

In embodiments, the invention provides methods for treating or preventing a disease or condition in a subject in need comprising administering to said subject an effective amount of the nanoparticle described herein.

In embodiments, the invention provides a process for making a nanoparticle comprising: a) combining an inner core comprising a non-cellular material, and an outer surface comprising a membrane derived from a cell that can be infected with a coronavirus; and b) exerting exogenous energy on the combination to form a nanoparticle comprising said inner core and said outer surface.

In embodiments, the invention provides a coronavirus-specific immunogenic composition comprising an effective amount of a nanoparticle comprising an inner core comprising a non-cellular material, and an outer surface comprising an outer membrane vesicle derived from a cell that can be infected with a coronavirus.

In embodiments, the invention provides a vaccine comprising the coronavirus-specific immunogenic composition described herein.

In embodiments, the invention provides methods for treating or preventing a coronavirus infection in a human subject in need comprising administering to said subject an effective amount of the coronavirus-specific immunogenic compositions described herein. In embodiments, the nanoparticle is administered via an oral, nasal, inhalational, parental, intravenous, intraperitoneal, subcutaneous, intramuscular, intradermal, topical, or rectal route.

In embodiments, the invention provides a that the nanoparticle substantially maintains natural structural integrity or activity of the cellular membrane or the constituents of the cellular membrane.

BRIEF DESCRIPTION OF THE DRAWINGS

FIG. 1 is a schematic of the invention. Under normal circumstances, the coronavirus infects the host cell by interacting with specific receptor(s) on the host cell. Cell membrane nanoparticles, or nanosponges, can be fabricated using the plasma membrane derived from cells that express the same receptor(s). Upon binding with the coronavirus, the nanosponges block entry of the coronavirus into healthy cells, thus rendering them biologically inactive.

DETAILED DESCRIPTION

Figure 1:
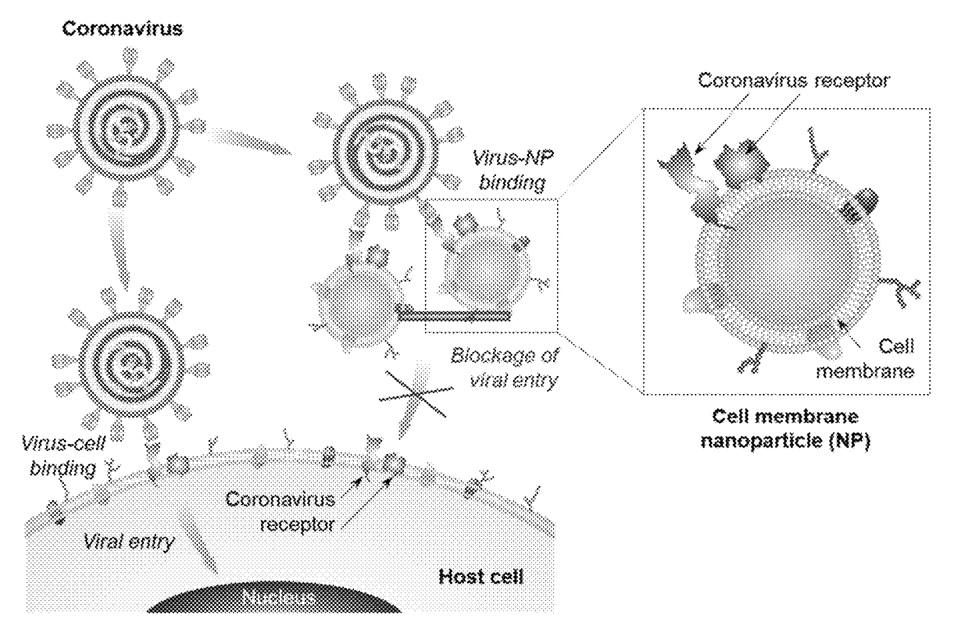

All publications, patents, and patent applications mentioned in this specification are herein incorporated by reference to the same extent as if each individual publication, patent, or patent application was specifically and individually indicated to be incorporated by reference.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the exemplary methods, devices, and materials are described herein.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, $2^{nd}$ ed. (Sambrook et al., 1989); Oligonucleotide Synthesis (M. J. Gait, ed., 1984); Animal Cell Culture (R. I. Freshney, ed., 1987); Methods in Enzymology (Academic Press, Inc.); Current Protocols in Molecular Biology (F. M. Ausubel et al., eds., 1987, and periodic updates); PCR: The Polymerase Chain Reaction (Mullis et al., eds., 1994); Remington, The Science and Practice of Pharmacy, $20^{th}$ ed., (Lippincott, Williams & Wilkins 2003), and Remington, The Science and Practice of Pharmacy, 22' ed., (Pharmaceutical Press and Philadelphia College of Pharmacy at University of the Sciences 2012).

This disclosure pertains to a new nanotechnology platform for treating respiratory viral infections, including coronavirus infections. The main active component of the platform is the plasma membrane derived from cells that are normally infected by a respiratory virus, such as coronaviruses. The membrane is used to fabricate nanoscale particles, termed "nanosponges," that can be easily administered via a number of different routes to patients. The nanosponges are capable of binding to and neutralizing coronaviruses because they express the surface receptors employed by the viruses for cellular entry. Notably, this approach for coronavirus treatment does not depend on preexisting knowledge of the molecular structure of individual coronaviruses. Instead, the working mechanism (receptor-mediated cellular entry) of all coronaviruses can be broadly targeted, thus providing a generalized solution against new outbreaks of coronavirus.

To fabricate nanosponges, the plasma membrane is collected from a source cell, normally by a differential centrifugation process. The source cell maybe a host cell that is normally infected by a respiratory virus, such as a coronavirus (e.g. a lung epithelial cell expressing ACE-2) or other virus. The cell can also be further modified physically, chemically and/or by genetic engineering, including to overexpress a receptor of interest.

Afterwards, the membrane material is processed into a nanoparticle by a process such as extrusion, sonication, or microfluidization, among others. It is possible to include a synthetic core within the center of the nanostructure, which can be used to load therapeutic payloads, including small molecule drugs, peptides, nucleic acids, and proteins, among many others.

These nanoparticles can be stored frozen, either in solution or after lyophilization, and thawed or reconstituted when treatment is required. Nanosponges work by displaying the same surface markers that the coronavirus normally uses to enter a host cell. Upon binding to the nanosponge, the coronavirus can no longer interact with healthy host cells, thus reducing their ability to propagate infections. The nanosponge-virus complex will then be taken up by phagocytic cells and safely broken down within the endolysosomal compartment. Due to their nanoscale size, nanosponges can be safely administered by a number of different routes, including subcutaneously, intradermally, intravenously, intratracheally, and intranasally, among others.

In embodiments, the invention provides a nanoparticle comprising an outer surface comprising a plasma membrane derived from a cell, including but not limited to, a lung epithelia cell expressing ACE-2 receptor, that can be infected with a respiratory virus, such as a coronavirus. Methods of manufacture and use for preventing or treating coronavirus infection in a subject in need are disclosed.

In embodiments, the nanoparticle further comprising an inner core comprising a non-cellular material. In embodiments, the cellular membrane is derived from a human lung epithelial cell. In embodiments, the cellular membrane comprises angiotensin-converting enzyme 2 (ACE-2) receptors, or other respiratory virus associated receptors such as shown in Table 1. In embodiments, the cellular membrane comprises a receptor that is not ACE-2. In embodiments, the cellular membrane is a: (i) genetically engineered cell membrane; (ii) physically and/or chemically modified cell membrane; and/or (iii) a hybrid membrane consisting of some natural cellular membrane and some synthetic lipid membranes. In embodiments, the cellular membrane has been genetically engineered to have increased expression of a receptor of interest, when compared with a cellular membrane that has not been genetically engineered.

It is understood that the methods of manufacture and use disclosed herein may be used to treat viruses other than coronavirus. The invention provides a nanoparticle comprising an outer surface comprising a plasma membrane derived from a cell, the source cell, that can be infected with a virus. The type of source cell depends on which virus the cellular nanosponge is used to treat. The cellular membrane derived from the source cell may comprise a receptor. Which receptor the cellular membrane comprises depends on which virus the cellular nanosponge is manufactured to target, i.e., treat. For example, if the plasma membrane on the outer surface of the nanoparticle comprises ICAM-1, the nanoparticle can be used to treat Rhinoviruses or Enteroviruses. Table 1 outlines some respiratory viruses and respiratory cellular receptors the plasma membrane may comprise in order to target those viruses.

TABLE 1

Respiratory Viruses

| Family (nucleic acid) | Key Viruses | Cellular receptors |
|---|---|---|
| Orthomyxoviridae | Influenza | Sialic acid |
| Paramyxoviridae | human respiratory syncytial virus (RSV) | Sialyl-glycoproteins, glycolipids |
| | Parainfluenza virus (PIV) | Sialyl-glycoproteins, glycolipids |
| | Human metapneumovirus (HMPV) | Sialyl-glycoproteins, glycolipids |
| Picornaviridae | Enteroviruses (coxsackievirus type A or B, echovirus) | ICAM-1, decay-accelerating factor (CD55), coxsackievirus and adenovirus receptor, integrins, ICAM-1, sialic acid |
| | Rhinovirus | ICAM-1, sialic acid |
| Coronaviridae | Human corona virus (HCoV) | |
| | HCoV 229E | CD13 |
| | HCoV NL63 | ACE2 |
| | SARS-CoV | ACE2 |
| | SARS-CoV-2 | ACE2 |
| | MERS-CoV | Sialic acid |
| Adenoviridae | Respiratory Adenovirus | coxsackievirus and adenovirus receptor, integrins |
| Parvoviridae | Human bocavirus (HBoV) | Likely sialyl-glycoproteins |

In embodiments, the nanoparticle further comprises a releasable cargo. In embodiments, the releasable cargo is a therapeutic agent, a prophylactic agent, a diagnostic or marker agent, a prognostic agent, or a combination thereof.

In embodiments, the invention provides medicament delivery systems, which comprising an effective amount of the nanoparticle described herein.

In embodiments, the invention provides pharmaceutical compositions comprising an effective amount of the nanoparticle described herein and a pharmaceutically acceptable carrier or excipient.

In embodiments, the invention provides methods for treating or preventing a disease or condition in a subject in need comprising administering to said subject an effective amount of the nanoparticle described herein. In embodiments, the disease or infection is a respiratory virus, such as those presented in Table 1. In embodiments, the respiratory virus is a coronavirus. In embodiments, the coronavirus is a HCoV, SARS, MERS, or SARS-CoV-2.

In embodiments, the invention provides a process for making a nanoparticle comprising: a) combining an inner core comprising a non-cellular material, and an outer surface comprising a membrane derived from a cell that can be infected with a respiratory virus, such as a coronavirus; and b) exerting exogenous energy on the combination to form a nanoparticle comprising said inner core and said outer surface.

In embodiments, the invention provides a coronavirus-specific immunogenic composition comprising an effective amount of a nanoparticle comprising an inner core comprising a non-cellular material, and an outer surface comprising an outer membrane vesicle derived from a cell that can be infected with a coronavirus.

In embodiments, the invention provides a vaccine comprising the respiratory virus-specific immunogenic composition described herein. In embodiments, the invention provides a vaccine comprising the coronavirus-specific immunogenic composition described herein.

In embodiments, the invention provides methods for treating or preventing a respiratory infection, such as but not limited to a coronavirus infection in a human subject in need comprising administering to said subject an effective amount of the coronavirus-specific immunogenic compositions described herein. In embodiments, the nanoparticle is administered via an oral, nasal, inhalational, parental, intravenous, intraperitoneal, subcutaneous, intramuscular, intradermal, topical, or rectal route.

In embodiments, the invention provides that the nanoparticle substantially maintains natural structural integrity or activity of the cellular membrane or the constituents of the cellular membrane.

A. Definitions

To facilitate understanding of the invention, a number of terms and abbreviations as used herein are defined below as follows:

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

Cellular Membrane: The term "cellular membrane" as used herein refers to a biological membrane enclosing or separating structure acting as a selective barrier, within or around a cell or an emergent viral particle. The cellular membrane is selectively permeable to ions and organic molecules and controls the movement of substances in and out of cells. The cellular membrane comprises a phospholipid uni- or bilayer, and optionally associated proteins and carbohydrates. As used herein, the cellular membrane refers to a membrane obtained from a naturally occurring biological membrane of a cell or cellular organelles, or one derived therefrom. As used herein, the term "naturally occurring" refers to one existing in nature. As used herein, the term "derived therefrom" refers to any subsequent modification of the natural membrane, such as isolating the cellular membrane, creating portions or fragments of the membrane, removing and/or adding certain components, such as lipid, protein or carbohydrates, from or into the membrane taken from a cell or a cellular organelle. A membrane can be derived from a naturally occurring membrane by any suitable methods. For example, a membrane can be prepared or isolated from a cell and the prepared or isolated membrane can be combined with other substances or materials to form a derived membrane. In another example, a cell can be recombinantly engineered to overexpress substances such as receptors and/or to produce "non-natural" substances that are incorporated into its membrane in vivo, and the cellular or viral membrane can be prepared or isolated from the cell or the virus to form a derived membrane. In embodiments, the cell membrane is derived from a cell that can be infected by a coronavirus, such as a respiratory cell or lung epithelial cell expressing ACE-2.

In various embodiments, the cellular membrane covering either of the unilamellar or multilamellar nanoparticles can be further modified to be saturated or unsaturated with other lipid components, such as cholesterol, free fatty acids, and phospholipids, also can include endogenous or added proteins and carbohydrates, such as cellular surface antigen. In such cases, an excess amount of the other lipid components can be added to the membrane wall which will shed until the concentration in the membrane wall reaches equilibrium, which can be dependent upon the nanoparticle environment. Membranes may also comprise other agents that may or may not increase an activity of the nanoparticle. In other examples, functional groups such as antibodies and aptamers can be added to the outer surface of the membrane to enhance site targeting, such as to cell surface epitopes found in cancer cells. The membrane of the nanoparticles can also comprise particles that can be biodegradable, cationic nanoparticles including, but not limited to, gold, silver, and synthetic nanoparticles.

Synthetic or artificial membrane: As used herein, the term “synthetic membrane” or “artificial membrane” refers to a man-made membrane that is produced from organic material, such as polymers and liquids, as well as inorganic materials. A wide variety of synthetic membranes are well known in the art.

Nanoparticle: The term “nanoparticle” as used herein refers to nanostructure, particles, vesicles, or fragments thereof having at least one dimension (e.g., height, length, width, or diameter) of between about 1 nm and about 10 m. For systemic use, an average diameter of about 50 nm to about 500 nm, or 100 nm to 250 nm may be preferred. The term “nanostructure” includes, but is not necessarily limited to, particles and engineered features. The particles and engineered features can have, for example, a regular or irregular shape. Such particles are also referred to as nanoparticles. The nanoparticles can be composed of organic materials or other materials, and can alternatively be implemented with porous particles. The layer of nanoparticles can be implemented with nanoparticles in a monolayer or with a layer having agglomerations of nanoparticles. In some embodiments, the nanoparticle comprising or consisting an inner core covered by an outer surface comprising the membrane as discussed herein. The invention contemplates any nanoparticles now known and later developed that can be coated with the membrane described herein.

Pharmaceutically active: The term “pharmaceutically active” as used herein refers to the beneficial biological activity of a substance on living matter and, in particular, on cells and tissues of the human body. A “pharmaceutically active agent” or “drug” is a substance that is pharmaceutically active and a “pharmaceutically active ingredient” (API) is the pharmaceutically active substance in a drug.

Pharmaceutically acceptable: The term “pharmaceutically acceptable” as used herein means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

Pharmaceutically acceptable salt: The term “pharmaceutically acceptable salt” as used herein refers to acid addition salts or base addition salts of the compounds, such as the multi-drug conjugates, in the present disclosure. A pharmaceutically acceptable salt is any salt which retains the activity of the parent nanoparticle or compound and does not impart any deleterious or undesirable effect on a subject to whom it is administered and in the context in which it is administered. Pharmaceutically acceptable salts may be derived from amino acids including, but not limited to, cysteine. Methods for producing compounds as salts are known to those of skill in the art (see, for example, Stahl et al., Handbook of Pharmaceutical Salts: Properties, Selection, and Use, Wiley-VCH; Verlag Helvetica Chimica Acta, Zurich, 2002; Berge et al., J Pharm. Sci. 66: 1, 1977). In some embodiments, a “pharmaceutically acceptable salt” is intended to mean a salt of a free acid or base of a nanoparticle or compound represented herein that is non-toxic, biologically tolerable, or otherwise biologically suitable for administration to the subject. See, generally, Berge, et al., J. Pharm. Sci., 1977, 66, 1-19. Preferred pharmaceutically acceptable salts are those that are pharmacologically effective and suitable for contact with the tissues of subjects without undue toxicity, irritation, or allergic response. A nanoparticle or compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosul fates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, [gamma]-hydroxybutyrates, glycolates, tartrates, and mandelates.

Pharmaceutically acceptable carrier: The term "pharmaceutically acceptable carrier" as used herein refers to an excipient, diluent, preservative, solubilizer, emulsifier, adjuvant, and/or vehicle with which a nanoparticle or compound, such as a multi-drug conjugate, is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy. 20" ed., (Lippincott, Williams & Wilkins 2003). Except insofar as any conventional media or agent is incompatible with the active compound, such use in the compositions is contemplated.

Phospholipid: The term "phospholipid", as used herein, refers to any of numerous lipids contain a diglyceride, a phosphate group, and a simple organic molecule such as choline. Examples of phospholipids include, but are not limited to, Phosphatide acid (phosphatidate) (PA), Phosphatidylethanolamine (cephalin) (PE), Phosphatidylcholine (lecithin) (PC), Phosphatidylserine (PS), and Phosphoinositides which include, but are not limited to, Phosphatidylinositol (PI), Phosphatidylinositol phosphate (PIP), Phosphatidylinositol bisphosphate (PIP2) and Phosphatidylinositol triphosphate (P1P3). Additional examples of PC include DDPC, DLPC, DMPC, DPPC, DSPC, DOPC, POPC, DRPC, and DEPC as defined in the art.

Therapeutically Effective Amount: As used herein, the term "therapeutically effective amount" refers to those amounts that, when administered to a particular subject in view of the nature and severity of that subject's disease or condition, will have a desired therapeutic effect, e.g., an amount which will cure, prevent, inhibit, or at least partially arrest or partially prevent a target disease or condition. More specific embodiments are included in the Pharmaceutical Preparations and Methods of Administration section below. In some embodiments, the term "therapeutically effective amount" or "effective amount" refers to an amount of a therapeutic agent that when administered alone or in combination with an additional therapeutic agent to a cell, tissue, or subject is effective to prevent or ameliorate the disease or condition such as a hemolytic disease or condition, or the progression of the disease or condition. A therapeutically effective dose further refers to that amount of the therapeutic agent sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously.

"Treating" or "treatment" or "alleviation" refers to therapeutic treatment wherein the object is to slow down (lessen) if not cure the targeted pathologic condition or disorder or prevent recurrence of the condition. A subject is successfully "treated" if, after receiving a therapeutic amount of a therapeutic agent, the subject shows observable and/or measurable reduction in or absence of one or more signs and symptoms of the particular disease. Reduction of the signs or symptoms of a disease may also be felt by the patient. A patient is also considered treated if the patient experiences stable disease. In some embodiments, treatment with a therapeutic agent is effective to result in the patients being disease-free 3 months after treatment, preferably 6 months, more preferably one year, even more preferably 2 or more years post treatment. These parameters for assessing successful treatment and improvement in the disease are readily measurable by routine procedures familiar to a physician of appropriate skill in the art.

As used herein, "preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition.

The term "combination" refers to either a fixed combination in one dosage unit form, or a kit of parts for the combined administration where a nanoparticle or compound and a combination partner (e.g., another drug as explained below, also referred to as "therapeutic agent" or "co-agent") may be administered independently at the same time or separately within time intervals, especially where these time intervals allow that the combination partners show a cooperative, e.g., synergistic effect. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g., a nanoparticle or compound and a combination partner, are both administered to a patient simultaneously in the form of a single entity or dosage. The term "non-fixed combination" means that the active ingredients, e.g., a nanoparticle or compound and a combination partner, are both administered to a patient as separate entities either simultaneously, concurrently or sequentially with no specific time limits, wherein such administration provides therapeutically effective levels of the two moieties or compounds in the body of the patient. The latter also applies to cocktail therapy, e.g., the administration of three or more active ingredients.

It is understood that aspects and embodiments of the invention described herein include "consisting" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein, a subject in need refers to an animal, a non-human mammal or a human. As used herein, "animals" include a pet, a farm animal, an economic animal, a sport animal and an experimental animal, such as a cat, a dog, a horse, a cow, an ox, a pig, a donkey, a sheep, a lamb, a goat, a mouse, a rabbit, a chicken, a duck, a goose, a primate, including a monkey and a chimpanzee.

Other objects, advantages and features of the present invention will become apparent from the following specification taken in conjunction with the accompanying drawings.

B. Nanoparticles and Uses Thereof

In one aspect, the present invention provides for a nanoparticle comprising: a) an inner core comprising a non-cellular material; and b) an outer surface comprising a cellular membrane that can be infected by a coronavirus. e.g., a human lung epithelial cell expressing for example ACE-2 receptors. In some embodiments, the membrane is a modified or processed membrane.

The present nanoparticle can comprise any suitable inner core. For example, the inner core of the present nanoparticle can comprise an inorganic substance, an organic substance, or an aggregate or a complex thereof. In another example, the inner core of the present nanoparticle can comprise a polymeric particle core, a silica particle core, or a metal, e.g., gold, particle core. In some embodiments, the inner core, e.g., the polymeric particle core, can comprise an optical shift property. In other embodiments, the inner core, e.g., the polymeric particle core, can comprise a metal, e.g., gold, iron oxide or a quantum dot. In still other embodiments, the inner core of the nanoparticle can comprise a biocompatible, a synthetic material or a polymer, such as poly(lactic-c-glycolic acid) (PLGA), polylactic acid (PLA), polyglycolic acid (PGA), polycaprolactone (PCL), polylysine, and polyglutamic acid. In yet other embodiments, the inner core of the present nanoparticle supports the outer surface.

The outer surface of the present nanoparticle can comprise any suitable modified or processed cellular membrane used by a coronavirus for infection. For example, the membrane can be modified or processed via any suitable physical, chemical or biological methods. In some embodiments, the membrane can be treated with enzyme(s), e.g., protease(s), to remove certain other proteins or peptides on the membrane.

In some embodiments, the nanoparticle can be configured as a vaccine, e.g., a coronavirus-specific vaccine. Preferably, the nanoparticle can be configured as a vaccine against a coronavirus such as COVID-19 and others. Also preferably, the vaccine further comprises an immunogenic adjuvant and/or potentiator.

The present nanoparticle can have any suitable size. For example, the present nanoparticle can have a diameter from about 10 nm to about 10 m. In certain embodiments, the diameter of the nanoparticle is about 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, 600 nm, 700 nm, 800 nm, 900 nm, 1 m, 2 m, 3 m, 4 m, 5 am, 6 am, 7 am, 8 am, 9 m, and 10 μm, or any sub-range within about 10 nm to about 10 μm, e.g., any range between any two of the above sizes. In some embodiments, the present nanoparticle can have a diameter from about 30 nm to about 60 nm, e.g., about 30-40 nm, 30-50 nm, 40-50 nm, 40-60 nm or 50-60 nm.

The present nanoparticle can have any suitable shape, including but not limited to, sphere, square, rectangle, triangle, circular disc, cube-like shape, cube, rectangular parallelepiped (cuboid), cone, cylinder, prism, pyramid, right-angled circular cylinder and other regular or irregular shape.

In some embodiments, the present nanoparticle can substantially lack constituents of the cell from which the cellular membrane is derived. For example, the present nanoparticle can lack at least 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the constituents of the cell from which the cellular membrane is derived. The present nanoparticle can lack any constituents of the cell from which the cellular membrane is derived. For example, the present nanoparticle can lack cell signaling biochemicals, DNA, RNA, proteins, endotoxins, and/or allied virulence molecules. The outer membrane preferably does include at least a portion of the cell, e.g. receptors, to which a coronavirus attaches to or infects the cell.

In some embodiments, the present nanoparticle can substantially maintain natural structural integrity or activity of the cellular membrane or the constituents of the cellular membrane derived from a cell. For example, the present nanoparticle can retain at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the natural structural integrity or activity for eliciting a specific immune response in a subject.

In some embodiments, the present nanoparticle can be biocompatible or biodegradable.

The outer surface of the present nanoparticle can further comprise a synthetic membrane. In some embodiments, the present nanoparticles comprise a mixture of nanoparticles that comprise an outer surface comprising a cellular membrane and nanoparticles that comprise an outer surface comprising a synthetic membrane. The nanoparticles that comprise an outer surface comprising a synthetic membrane may or may not be capable of eliciting a coronavirus-specific immune response in a subject. In some embodiments, both the nanoparticles that comprise an outer surface comprising a membrane and nanoparticles that comprise an outer surface comprising a synthetic membrane are capable of eliciting a coronavirus-specific immune response in a subject.

The present nanoparticles can comprise the nanoparticles that comprise an outer surface comprising a membrane and nanoparticles that comprise an outer surface comprising a synthetic membrane in any suitable ratio. In some embodiments, The present nanoparticles can comprise at least about 1% (w/w), 2% (w/w), 3% (w/w), 4% (w/w), 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w), 96% (w/w), 97% (w/w), 98% (w/w), 99% (w/w), or more of the nanoparticles that comprise an outer surface comprising a membrane. In other embodiments, the present nanoparticles can comprise at least about 1% (w/w), 2% (w/w), 3% (w/w), 4% (w/w), 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w), 96% (w/w), 97% (w/w), 98% (w/w), 99% (w/w), or more of the nanoparticles that comprise an outer surface comprising a synthetic membrane. For example, the present nanoparticles can comprise about 1-10% (w/w) of the nanoparticles that comprise an outer surface comprising a membrane and about 90-99% (w/w) of the nanoparticles that comprise an outer surface comprising a synthetic membrane, about 11-25% (w/w) of the nanoparticles that comprise an outer surface comprising a membrane and about 75-89% (w/w) of the nanoparticles that comprise an outer surface comprising a synthetic membrane, about 50% (w/w) of the nanoparticles that comprise an outer surface comprising a membrane and about 50% (w/w) of the nanoparticles that comprise an outer surface comprising a synthetic membrane, about 51-75% (w/w) of the nanoparticles that comprise an outer surface comprising a membrane and about 49-25% (w/w) of the nanoparticles that comprise an outer surface comprising a synthetic membrane, or about 90-100% (w/w) of the nanoparticles that comprise an outer surface comprising a membrane and about 0-10% (w/w) of the nanoparticles that comprise an outer surface comprising a synthetic membrane.

The outer surface of the present nanoparticle can comprise a hybrid membrane comprising a cellular membrane derived from a cell that can be infected with coronavirus and a synthetic membrane. In some embodiments, the outer surface of the nanoparticle can comprise a hybrid membrane comprising at least about 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w), 96% (w/w), 97% (w/w), 98% (w/w), 99% (w/w) of a cellular membrane derived from a cell that can be infected with coronavirus. In other embodiments, the outer surface of the nanoparticle can comprise a hybrid membrane comprising at least about 1% (w/w), 2% (w/w), 3% (w/w), 4% (w/w), 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w) of a synthetic membrane. For example, the outer surface of the nanoparticle can comprise a hybrid membrane comprising about 5-10% (w/w) of a cellular membrane derived from a cell that can be infected with coronavirus and about 95-99% (w/w) of a synthetic membrane, about 11-25% (w/w) of a cellular membrane derived from a cell that can be infected with coronavirus and about 75-89% (w/w) of a synthetic membrane, about 50% (w/w) of a cellular membrane derived from a bacterium and about 50% (w/w) of a synthetic membrane, about 51-75% (w/w) of a cellular membrane derived from a cell that can be infected with coronavirus and about 49-25% (w/w) of a synthetic membrane, or about 90-99% (w/w) of a cellular membrane derived from a cell that can be infected with coronavirus and about 1-10% (w/w) of a synthetic membrane.

The present nanoparticle can comprise a releasable cargo at any suitable location. For example, the releasable cargo can be located within or on the inner core, between the inner core and the outer surface, or within or on the outer surface. The release of the releasable cargo can be triggered by any suitable mechanisms. For example, the release of the releasable cargo can be triggered by a contact between the nanoparticle and the subject or cells of the subject, or by a change of a physical parameter surrounding the nanoparticle, including contact with a coronavirus. The nanoparticle can comprise any suitable type of a releasable cargo. For example, the releasable cargo can be a metallic particle, a polymeric particle, a dendrimer particle, or an inorganic particle.

The releasable cargo can comprise any suitable substance or agent, e.g., a therapeutic agent, a prophylactic agent, a diagnostic or marker agent, a prognostic agent, an isolation agent, a monitoring agent, or a combination thereof. The therapeutic agent or prophylactic agent can be any suitable substance or agent, e.g., an anti-viral agent, an antibiotic, an anti-fungal agent, or an anti-protozoa agent. In some embodiments, the therapeutic agent or prophylactic agent is quinine.

In some embodiments, the therapeutic agent or prophylactic agent is an antibiotic. Any suitable antibiotic can be used. For example, the antibiotic can have a bactericidal activity or bacteriostatic activity. In another example, the antibiotic can be a narrow-spectrum or a broad-spectrum antibiotic. In still another example, the antibiotic can target the bacterial cell wall (e.g., penicillins and cephalosporins), can target the cell membrane (e.g., polymyxins), can interfere with essential bacterial enzymes (e.g., rifamycins, lipiarmycins, quinolones and sulfonamides), targets protein synthesis (e.g., macrolides, lincosamides and tetracyclines), or can be a cyclic lipopeptide (such as daptomycin), a glycylcycline (such as tigecycline), an oxazolidinone (such as linezolid), or a lipiarmycin (such as fidaxomicin).

In other embodiments, the antibiotic can be an inhibitor of cell wall synthesis, an inhibitor of protein synthesis, an inhibitor of membrane function, an inhibitor for folate pathway, or an inhibitor of nucleic acid synthesis function. Any suitable inhibitor of cell wall synthesis can be used. For example, the inhibitor of cell wall synthesis can be penicillin, cephalosporin, monobactam, penem, a glycopeptide, or a lipoglycopeptide.

In some embodiments, the present nanoparticle can further comprise exemplary antibiotic(s), or a combination thereof, listed in the following Table 2.

TABLE 2

Exemplary Antibiotics

| | International Common Name Examples |
|---|---|
| Beta-lactams (Penicillins) - Inhibitors of Cell Wall Synthesis | |
| Penicillins (pen G) | Penicillin G |
| Penicillinase-stable penicillins (pen M) | Oxacillin |
| | Methicillin |
| Aminopenicillins (pen A) | Ampicillin |
| Penicillinase labile: hydrolyzed by staphylococcal penicillinase | Amoxicillin |
| Carboxypenicillins (pen C) | Ticarcillin |
| Ureidopenicillins (pen U) | Piperacillin |
| Beta-lactam/Beta-lactamase inhibitor combinations | Amoxicillin + clavulanic acid |
| | Ampicillin + sulbactam |
| | Ticarcillin + clavulanic acid |
| | Piperacillin + tazobactam |
| Amidinopenicillin | Mecillinam |
| Beta-lactams (Cephems) - Inhibitors of Cell Wall Synthesis | |
| 1st Generation Cephalosporins C1G | Cephalothin |
| | Cefazolin |
| 2nd Generation Cephalosporins C2G | Cefuroxime |
| | Cefamandole |
| | Cephamycin (new C2G) |
| | Cefoxitin |
| | Cefotetan - |
| 3rd Generation Cephalosporins C3G | Cefotaxime |
| | Ceftazidime |
| | Ceftriaxone |
| 4th Generation Cephalosporins C4G Oral C3G | Cefepime |
| Next Generation Cephalosporins (Anti-MRSA) | Ceftobiprole |
| | Ceftaroline |
| Beta-lactams-Inhibitors of Cell Wall Synthesis | |
| Monobactams | Aztreonam |
| Penems | Imipenem |
| -Carbapenems | Meropenem |
| Penems | Etrapenem |
| | Doripenem |
| | Faropenem |
| Glycopeptides - Inhibitors of Cell Wall Synthesis | |
| Glycopeptides | Vancomycin |
| Lipoglycopeptides | Dalbavancin |
| | Oritavancin |
| | Teavanacin |
| | Teicoplanin |
| Inhibitors of Protein Synthesis | |
| Aminoglycosides - (Bactericidal) | Gentamicin |
| | Streptomycin |
| | Tobramycin |
| | Kanamycin |
| | Amikacin |
| Macrolide-lincosamide-streptogramin-ketolide-(MLSK) (Bacteriostatic) | Erythromycin |
| | Clindamycin |
| | Quinupristin-Dalfopristin (Synercid) |
| | Clarithromycin |
| | Azithromycin |
| | Telithromycin |
| Tetracyclines - (Bacteriostatic) | Tetracycline |
| | Doxycycline |
| | Minocycline |
| Glycylcyclines | Tigecycline |
| Phenocols (Bacteriostatic) | Chloramphenicol |
| Oxazolidinones (Bactericidal for Streptococci; Bacteriostatic for Enterococcus and Staphylococci) | Linezolid |
| Ansamycins ((Bacteriostatic or Bactericidal depending on organism and concentration) Inhibitors of Membrane Function | Rifampin |
| Lipopeptides | Polymyxin B |
| | Colistin |
| Cyclic Lipopeptides | Daptomycin |
| Antimetabolites- Folate Pathway Inhibitors | |
| Sulfonamides (Bactericidal)- Inhibits pteridine synthase and dihydrofolic acid reductase Inhibitors of Nucleic Acid Synthesis Function | Trimethoprim/ Sulfamethoxazole |
| Fluoroquinolones (Bactericidal)- Inhibits DNA Gyrase and Topoisomerase | Ciprofloxacin |
| | Levofloxacin |
| | Gatifloxacin |
| | Moxifloxacin |
| | Garenoxacin |
| | Lomefloxacin |
| | Norfloxacin |
| | Sparfloxacin |
| Quinolones First Generation- Narrow spectrum (Only gram negatives) | Nalidixic Acid |
| | Cinoxacin |
| Furanes (Bactericidal)- Gram positive and gram negative urinary tract infections | Nitrofurantoin |

(Adapted from Biomerieux Vitek 2 Customer Education March 2008-<http://www.biomerieux-usa.com/upload/VITEK-Bus-Module-1-Antibiotic-Classification-and-Modes-of-Action-1.pdf>).

In some embodiments, the membrane in the outer surface of the present nanoparticle has a protein loading yield, defined as the weight ratio of immobilized proteins to the nanoparticle, of at least from about 1 wt % to about 95 wt %, or more, e.g., at least about 1 wt %, 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 20 wt %, 30 wt %, 40 wt %, 50 wt %, 60 wt %, 70 wt %, 80 wt %, 90 wt %, 95 wt %, or more.

In some embodiments, the present nanoparticle is substantially stable, e.g., not aggregating, in a biological or physiological solution or environment, e.g., biological buffer or in vivo environment. For example, at least 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the present nanoparticles do not aggregate in a biological or physiological solution or environment, e.g., biological buffer or in vivo environment, for at least 1 minute, 2 minutes, 3 minutes, 4 minutes, 5 minutes, 6 minutes, 7 minutes, 8 minutes, 9 minutes, 10 minute, 20 minutes, 30 minutes, 40 minutes, 50 minutes, 1 hour, 2 hours, 3 hours, 4 hours, 5 hours, 6 hours, 7 hours, 8 hours, 9 hours, 10 hours, 16 hours, 1 day, 2 days, 3 days, 4 days, 5 days, 6 days, 1 week or longer.

In some embodiments, the present nanoparticle substantially maintains its size in a biological or physiological solution or environment, e.g., biological buffer or in vivo environment. For example, at least 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the present nanoparticles maintain their sizes in a biological or physiological solution or environment, e.g., biological buffer or in vivo environment, for at least 1 hour, 2 hours, 3 hours, 4 hours, 5 hours, 6 hours, 7 hours, 8 hours, 9 hours, 10 hours, 16 hours, 1 day, 2 days, 3 days, 4 days, 5 days, 6 days, 1 week or longer.

In some embodiments, the outer surface of the present nanoparticle substantially shields inner core. For example, the outer surface of the present nanoparticle shields at least 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the inner core.

In some embodiments, the outer surface of the present nanoparticle is configured not to be substantially replaced by a reactive agent, e.g., a thiol containing agent. For example, at least 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the outer surface of the present nanoparticle is configured not to be substantially replaced by a reactive agent, e.g., a thiol containing agent.

In some embodiments, the present nanoparticle is configured to elicit an immune response to the constituents of the membrane from which the membrane in the outer surface is derived.

In some embodiments, the present nanoparticle is configured to elicit a humoral immune response to the constituents of the membrane from which the membrane is derived. The present nanoparticle can also be configured to generate an antibody having a higher avidity than that of an antibody generated by a comparable outer membrane.

In some embodiments, the present nanoparticle is configured to elicit a cellular immune response, e.g., T cell response, to the constituents of the membrane from which the membrane in the outer surface is derived. For example, the present nanoparticle can be configured to elicit a stronger cellular immune response than that generated by a comparable outer membrane. For example, the present nanoparticle can also be configured to induce or enhance expression of a cytokine associated with T cell activation. The exemplary cytokines include interferon gamma (IFNγ), interleukin 17 (IL-17) and interleukin 4 (IL-4).

In some embodiments, the membrane, e.g., the membrane derived from a cell that can be infected with a coronavirus, of the present nanoparticle comprises a modification. The modification can be made by any suitable ways. For example, the modification can be made by physical, chemical and/or biological methods. In some embodiments, the modification can be made by genetic engineering or enzymatic treatment(s), protease treatment(s). The membrane of the present nanoparticle can be modified to comprise any suitable substance. For example, the membrane can be modified to comprise a mutant or an exogenous antigen.

In some embodiments, the present disclosure provides for a medicament delivery system, which comprises an effective amount of the present nanoparticle. The medicament delivery system can further comprise another active ingredient, and/or a medically and/or pharmaceutically acceptable carrier or excipient.

In some embodiments, the present disclosure provides for a pharmaceutical composition, which pharmaceutical composition comprises an effective amount of the present nanoparticle and a pharmaceutically acceptable carrier or excipient. The pharmaceutical composition can further comprise another active ingredient, e.g., an antibiotic or antiviral agent.

The present disclosure provides for a method for treating and/or preventing a disease or condition in a subject, which method comprises administering, to a subject in need of such treatment and/or prevention, an effective amount of the present nanoparticle, the present medicament delivery system, or the present pharmaceutical composition. The present method can be used to treat and/or prevent any suitable disease or condition in a subject. In some embodiments, the disease or condition is viral infection. In some embodiments, the virus is a respiratory virus. In some embodiments, the respiratory virus is a coronavirus, including but not limited to, SARS-CoV-2.

The present method can be used to treat and/or prevent a disease or condition in any suitable subject. For example, the present method can be used to treat and/or prevent a disease or condition in a human or a non-human mammal. The present method can further comprise administering another active ingredient to the subject and/or a pharmaceutically acceptable carrier or excipient to the subject. The present nanoparticle can also be administered via a medicament delivery system. The present nanoparticle, medicament delivery system and/or pharmaceutical composition can be administered via any suitable route. For example, the present nanoparticle, medicament delivery system and/or pharmaceutical composition can be administered via an oral, nasal, inhalational, parental, intravenous, intraperitoneal, subcutaneous, intramuscular, intradermal, topical, or rectal route.

In another aspect, the present invention is directed to use of an effective amount of the present nanoparticle for the manufacture of a medicament for treating and/or preventing a disease or condition in a subject.

In some embodiments, the present methods are used to treat viral infection in a subject. In other embodiments, the present methods are used to prevent coronavirus infection in a subject or to protect a subject from viral infection.

C. Processes for Making a Nanoparticle

In still another aspect, the present invention provides for a process for making a nanoparticle, which process comprises mixing a nanoparticle inner core comprising a non-cellular material with a membrane, e.g., a cellular membrane derived from a cell that can be infected with a coronavirus, while exerting exogenous energy to form a nanoparticle comprising said inner core and an outer surface comprising said membrane.

Any suitable exogenous energy can be used. For example, the exogenous energy can be a mechanical energy, an acoustic energy and/or a thermal energy. In some embodiments, the mechanical energy can be exerted by extrusion. In some embodiments, the acoustic energy can be exerted by sonication. In some embodiments, the thermal energy can be exerted by heating.

The outer membrane can be prepared by any suitable methods. For example, the cell membranes can be isolated by filtration or a low-speed centrifugation, e.g., centrifugation conducted at about 3,000×g to about 8,000×g. For example, the centrifugation can be conducted at about 3,000×g, 4,000×g, 5,000×g, 6,000×g, 7,000×g, or 8,000×g.

The present process can further comprise concentrating the outer membrane. The outer membrane can be concentrated by any suitable methods. For example, the outer membrane can be concentrated by filtration.

The outer membrane can be collected by any suitable methods. In some embodiments, the bacteria outer membrane can be collected by a high-speed centrifugation, e.g., high-speed centrifugation conducted at about 10,000×g to about 300,000×g. For example, the centrifugation can be conducted at about 10,000×g, 50,000×g, 100,000×g, 110,000×g, 120,000×g, 130,000×g, 140,000×g, 150,000×g, 160,000×g, 170,000×g, 180,000×g, 190,000×g, 200,000×g, 210, 000×g, 220,000×g, 230,000×g, 240,000×g, 250,000×g, 260,000×g, 270,000×g, 280,000×g, 290,000×g, or 300,000×g.

Nanoparticles made by the present process are also provided. The nanoparticles made by the present process can be used for any suitable purpose. For example, an effective amount of the nanoparticles made by the present process can be used for the manufacture of a medicament for treating and/or preventing a disease or condition, e.g., coronavirus infection, in a subject.

D. Pharmaceutical Compositions and Administration Routes

The pharmaceutical compositions comprising the present nanoparticles, alone or in combination with other active ingredient(s), described herein may further comprise one or more pharmaceutically-acceptable excipients. A pharmaceutically-acceptable excipient is a substance that is non-toxic and otherwise biologically suitable for administration to a subject. Such excipients facilitate administration of the nanoparticles, alone or in combination with other active ingredient(s), described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the various embodiments are sterile compositions. Pharmaceutical compositions may be prepared using compounding techniques known or that become available to those skilled in the art.

Sterile compositions are within the present disclosure, including compositions that are in accord with national and local regulations governing such compositions.

The pharmaceutical compositions and the nanoparticles, alone or in combination with other active ingredient(s), described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. The nanoparticles, alone or in combination with other active ingredient(s), described herein, and preferably in the form of a pharmaceutical composition, may be administered by a suitable route of delivery, such as oral, parenteral, rectal, nasal, topical, or ocular routes, or by inhalation. In some embodiments, the compositions are formulated for intravenous or oral administration.

For oral administration, the nanoparticles, alone or in combination with another active ingredient, may be provided in a solid form, such as a tablet or capsule, or as a solution, emulsion, or suspension. To prepare the oral compositions, the nanoparticles, alone or in combination with other active ingredient(s), may be formulated to yield a dosage of, e.g., from about 0.01 to about 50 mg/kg daily, or from about 0.05 to about 20 mg/kg daily, or from about 0.1 to about 10 mg/kg daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil, such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The compositions may be formulated for rectal administration as a suppository. For parenteral use, including intravenous, intramuscular, intraperitoneal, intranasal, or subcutaneous routes, the nanoparticles, alone or in combination with other active ingredient(s), may be provided in sterile aqueous solutions or suspensions, buffered to an appropriate pH and isotonicity or in parenterally acceptable oil. Suitable aqueous vehicles can include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 g/kg/minute of agent admixed with a pharmaceutical carrier over a period ranging from several minutes to several days.

For nasal, inhaled, or oral administration, the nanoparticles, alone or in combination with other active ingredient(s), may be administered using, for example, a spray formulation also containing a suitable carrier.

For topical applications, the nanoparticles, alone or in combination with other active ingredient(s), are preferably formulated as creams or ointments or a similar vehicle suitable for topical administration. For topical administration, the nanoparticles, alone or in combination with other active ingredient(s), may be mixed with a pharmaceutical carrier at a concentration of about 0.1% to about 10% of drug to vehicle. Another mode of administering the nanoparticles, alone or in combination with other active ingredient(s), may utilize a patch formulation to effect transdermal delivery.

In certain embodiments, the present disclosure provides pharmaceutical composition comprising the nanoparticles, alone or in combination with other active ingredient(s), and methylcellulose. In certain embodiments, methylcellulose is in a suspension of about 0.1, 0.2, 0.3, 0.4, or 0.5 to about 1%. In certain embodiments, methylcellulose is in a suspension of about 0.1 to about 0.5, 0.6, 0.7, 0.8, 0.9, or 1%. In certain embodiments, methylcellulose is in a suspension of about 0.1 to about 1%. In certain embodiments, methylcellulose is in a suspension of about 0.1, 0.2, 0.3, 0.4, 0.5, 0.6, 0.7, 0.8, 0.8, or 1%. In certain embodiments, methylcellulose is in a suspension of about 0.5%.

What is claimed is:

1. A nanoparticle comprising an outer surface comprising a plasma membrane derived from a human lung epithelial cell or macrophage that can be infected with a respiratory virus.

2. The nanoparticle of claim 1, further comprising an inner core comprising a non-cellular material.

3. The nanoparticle of claim 1, wherein the plasma membrane is derived from the human lung epithelial cell.

4. The nanoparticle of claim 1, wherein the plasma membrane comprises angiotensin-converting enzyme 2 (ACE-2) receptors.

5. The nanoparticle of claim 1, wherein the nanoparticle further comprises a releasable cargo.

6. The nanoparticle of claim 5, wherein the releasable cargo is a therapeutic agent, a prophylactic agent, a diagnostic or marker agent, a prognostic agent, or a combination thereof.

7. The nanoparticle of claim 1, wherein the respiratory virus is a coronavirus.

8. The nanoparticle of claim 7, wherein the coronavirus is SARS-CoV-2.

9. A medicament delivery system, which comprises an effective amount of the nanoparticle of claim 1.

10. A pharmaceutical composition comprising an effective amount of the nanoparticle of claim 1 and a pharmaceutically acceptable carrier or excipient.

11. A method for treating a disease or condition in a subject in need thereof comprising administering to said subject an effective amount of the nanoparticle of claim 1, wherein the disease or condition is a coronavirus infection.

12. A process for making a nanoparticle comprising:
a) combining an inner core comprising a non-cellular material, and an outer surface comprising a membrane derived from a human lung epithelial cell or macrophage that can be infected with a respiratory virus; and
b) exerting exogenous energy on the combination to form a nanoparticle comprising said inner core and said outer surface.

13. The process for making a nanoparticle of claim 12, wherein the respiratory virus is a coronavirus.

14. The process for making a nanoparticle of claim 12, wherein the membrane derived from a cell is genetically modified.

15. A coronavirus-specific composition comprising an effective amount of a nanoparticle comprising an inner core comprising a non-cellular material, and an outer surface comprising an outer membrane vesicle derived from a human lung epithelial cell or macrophage that can be infected with a coronavirus.

16. A method for treating a coronavirus infection in a human subject in need thereof comprising administering to said subject an effective amount of the coronavirus-specific composition of claim 15.

17. The method of claim 16, wherein the nanoparticle is administered via an oral, nasal, inhalational, parenteral, intravenous, intraperitoneal, subcutaneous, intramuscular, intradermal, topical, or rectal route.

18. The method of claim 16, wherein the nanoparticle substantially maintains natural structural integrity or activity of the cellular membrane or the constituents of the cellular membrane.

19. The method of claim 18, wherein the coronavirus is SARS-CoV-2.

20. The nanoparticle of claim 1, wherein the plasma membrane does not comprise any portion of the respiratory virus.

* * * * *